United States Patent [19]

Thorne et al.

[11] 4,036,844
[45] July 19, 1977

[54] ARYLOXYPYRIDINES

[75] Inventors: David Edward Thorne, Cranleigh, England; Kurt Engel, Basel, Switzerland

[73] Assignee: Beecham Group Limited, England

[21] Appl. No.: 626,720

[22] Filed: Oct. 29, 1975

Related U.S. Application Data

[63] Continuation of Ser. No. 346,252, March 30, 1973, abandoned.

[30] Foreign Application Priority Data

Apr. 4, 1972 United Kingdom ............... 15280/72
Dec. 23, 1974 United Kingdom ............... 55441/74

[51] Int. Cl.² .......................................... C07D 213/55
[52] U.S. Cl. ........................... 260/295 R; 260/294.9;
260/295 AM; 260/295.5 R; 260/295.5 A;
260/297 R; 424/263
[58] Field of Search ................... 260/295.5 R, 295 R,
260/295.5 A, 295 AM, 297 R, 294.9

[56] References Cited

FOREIGN PATENT DOCUMENTS 4,512,319  5/1970  Japan ............................... 260/295 R

OTHER PUBLICATIONS

Burger, Medicinal Chemistry, Second Edition, Interscience Publishers, p. 497.
Shindo et al., Chem. Abstracts, vol. 77 (21) Item 136214v, Nov. 20, 1972.

Primary Examiner—Alan L. Rotman
Attorney, Agent, or Firm—Jacobs & Jacobs

[57] ABSTRACT

Compounds of the formula

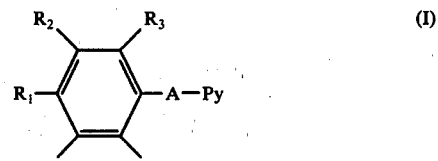

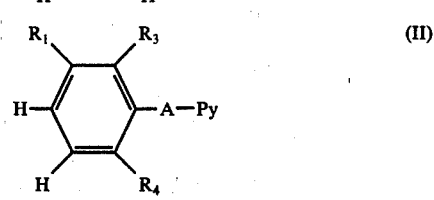

wherein
Py is a substituted or unsubstituted 2-, 3- or 4-pyridyl, N-oxidized or quaternized pyridyl group;
A is a group of the formula (IIIA), (IIIB) or (IIIC)

$-[ALK-O]-$  $-[O-ALK]-$  $-[ALK-O-ALK]-$
(IIIA)        (IIIB)        (IIIC)

wherein
ALK is straight or branched chain alkylene of 1 to 6 carbon atoms;
$R_1$ is a carboxylic acid group, a group which is converted in the human body to a carboxylic acid group or acyl; $R_2$, $R_3$ and $R_4$ are each hydrogen, a carboxylic acid group, a group which is converted in the human body to a carboxylic acid group, acyl, hydroxy, alkoxy, aralkoxy, aryloxy, an esterified hydroxy group, nitro, halogen or amino;

may be formulated into pharmaceutical compositions useful for the treatment of hyperglycaemia by combining said compounds with a pharmaceutically acceptable non-toxic inert diluent or carrier.

Compounds of the formula

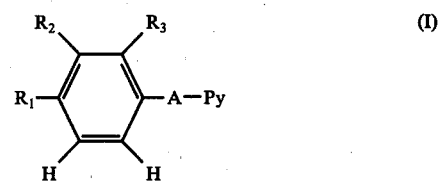

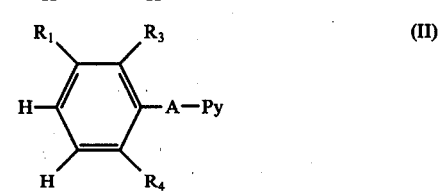

wherein
Py is a substituted or unsubstituted 2-, 3- or 4-pyridyl, N-oxidized or quaternized pyridyl group;
A is a group of formula (IIIA), (IIIB) or (IIIC)

$-[ALK-O]-$  $-[O-ALK]-$  $-[ALK-O-ALK]-$
(IIIA)        (IIIB)        (IIIC)

wherein
ALK is straight or branched chain alkylene of 1 to 6 carbon atoms;
$R_1$ is a carboxylic acid group, a group which is converted in the human body to a carboxylic acid group or acyl;
$R_2$, $R_3$ and $R_4$ are each hydrogen, a carboxylic acid group, a group which is converted in the human body to a carboxylic acid group, hydroxy, alkoxy, aralkoxy, aryloxy, an esterified hydroxy group, nitro, halogen, or amino,
provided that $R_1$ is not methyl, cyano or methoxycarbonyl when Py is 2-pyridyl or 5-ethylpyrid-2-yl and A is $-[O-CH_2]-$ and $R_2$, $R_3$ and $R_4$ are hydrogen or halogen, are novel compounds per se.

The compounds and compositions above described are useful for their hypoglycaemic activity and are useful in the treatment of hypoglycaemic conditions such as diabetes milletus.

8 Claims, No Drawings

ARYLOXYPYRIDINES

CROSS-REFERENCE

This is a continuation of Ser. No. 346,252 filed Mar. 30, 1973, now abandoned.

This invention relates to compounds which have hypoglycaemic activity and which are therefore of value in the treatment of hyperglycaemic conditions such as diabetes mellitus. Many of the compounds also have hypolipidaemic activity. The invention also relates to pharmaceutical compositions comprising such compounds and to a method for the preparation of the compounds.

Present oral antidiabetic therapy involves the administration of either sulphonyl ureas or biguanides. The former class of compound exert their effect by releasing insulin from the pancreas while the latter class of compound inhibit glucose uptake from the small intestine, inhibit hepatic gluconeogenesis and under certain conditions increase peripheral glucose utilisation.

In our search for new agents for the treatment of diabetes mellitus which have advantages over the previously available sulphonylureas and biguanides, we have noted a class of basic ethers. Preliminary tests showed that hypoglycaemic activity in alloxanised mice was a characteristic of the class as a whole and subsequent tests in normal mice and other species including rate, guinea pigs and squirrel monkeys, confirmed these preliminary findings.

The compounds which we found to have hypoglycaemic activity were those of formula (I) or formula (II) and acid addition salts thereof:

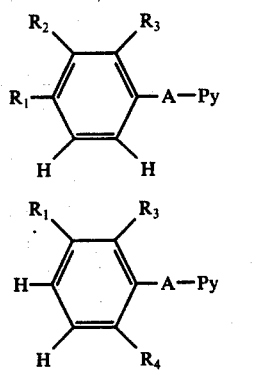

in which formulae Py represents a substituted or unsubstituted 2-, 3- or 4- pyridyl, N-oxidised or quaternised pyridyl group; A represents a group of formula (IIIA), (IIIB) or (IIIC)

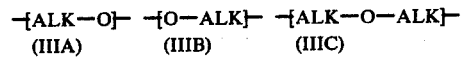

wherein ALK represents a straight or branched chain alkylene group having from 1 to 6 carbon atoms; $R_1$ represents a carboxylic acid group, a group which is converted in the human body to a carboxylic acid group or an acyl group; $R_2$, $R_3$ and $R_4$ each separately represent hydrogen, a carboxylic acid group, a group which is converted in the human body to a carboxylic acid group, an acyl group, a hydroxy group, an alkoxy group, an aralkoxy group, an aryloxy group, an esterified hydroxy group, a nitro group, a halogen group or an amino group.

However, a search of the chemical literature has shown that not all compounds of formula (I) or (II) are novel. The known compounds are those of formula (I) or (II) wherein Py is 2-pyridyl or 5-ethylpyrid-2-yl, A is $-(O-CH_2)-$ $R_1$ is methyl, cyano or methoxycarbonyl and $R_2$, $R_3$ and $R_4$ are separately hydrogen or halogen. The only reported activity of this known class of compounds is insecticidal or fungicidal activity. It will therefore be clear that the discovery that compounds of formula (I) and (II) above have hypoglycaemic activity is a new and unexpected one, and that pharmaceutical compositions comprising such compounds are not foreshadowed in any way by the prior art.

Thus, in its broadest aspect, the present invention provides a pharmaceutical composition, useful in the treatment of hyperglycaemia, comprising a compound of formula (I) or (II) as defined above, or an acid addition salt thereof and one or more pharmaceutically acceptable carriers.

As is common practice, such compositions will usually be accompanied by or associated with written or printed directions, for use in the medical treatment concerned, in this case as an agent for reducing serum sugar levels.

In preparing the pharmaceutical compositions of this invention, the compound is incorporated in a suitable carrier such as a pharmaceutical carrier, a beverage or a foodstuff. The compositions may be in the form of tablets, linguets, powders, capsules, slurries, troches or lozenges. The choice of carrier will be governed by the desired properties of the composition and normal pharmaceutical practice may be followed. Thus, in formulating solid compositions carriers such as mangesium salts, starch, lactose, talc and chalk may be used. The composition may also be in the form of an ingestible capsule (e.g. of gelatin) to contain the compound; or in the form of a syrup, a liquid solution or a suspension. Suitable liquid pharmaceutical carriers include ethyl alcohol, glycerine, saline, and water, and if desired conventional flavouring or colouring agents may be present. The compound may also, if desired, be incorporated in a foodstuff, e.g. in the form of a biscuit.

Since the majority of compounds of formula (I) and (II) above are new compounds, this invention includes, in another of its aspects, these new compounds, i.e. compounds of formula (I) or formula (II) and acid addition salts thereof:

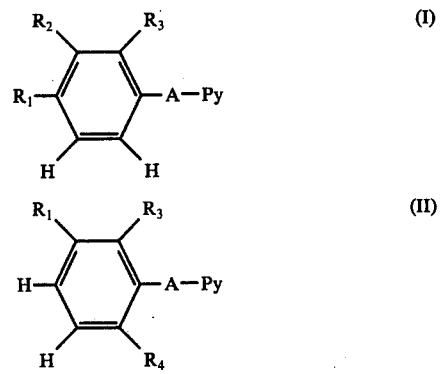

in which formulae Py represents a substituted or unsubstituted 2-, 3- or 4-pyridyl, N-oxidised or quaternised pyridyl group; A represents a group of formula (IIIA), (IIIB) or (IIIC).

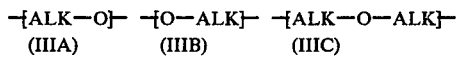

wherein ALK represents a straight or branched chain alkylene group having 1 to 6 carbon atoms; $R_1$ represents a carboxylic acid group, a group which is converted in the human body to a carboxylic acid group or an acyl group; $R_2$, $R_3$ and $R_4$ each separately represent hydrogen, a carboxylic acid group, a group which is converted in the human body to a carboxylic acid group, an acyl group, a hydroxy group, an alkoxy group, an aralkoxy group, an aryloxy group, an esterified hydroxy group, a nitro group, a halogen group or an amino group, provided that $R_1$ is not methyl, cyano or methoxycarbonyl when Py is 2-pyridly or 5-ethylpyrid-2-yl and A is $[O-CH_2]$ and $R_2$, $R_3$ and $R_4$ are hydrogen or halogen.

In the above definition the divalent radical A which links the phenyl and pyridyl rings has been defined as a group of formula (IIIA), (IIIB) or (IIIC). The symbol ALK preferably represents a methylene, ethylene, or n-propylene group, but straight or branched chain alkylene groups having from 1 to 6 carbon atoms are in general suitable.

Also in the definition of the compounds of this invention, the symbol Py has been defined as a substituted or unsubstituted 2-, 3- or 4-pyridyl, N-oxidised or quaternised pyridyl group. We have noted a tendency for N-oxidation or quaternisation to reduce the hypoglycaemic activity of the compounds of this invention, and thus it is preferred that Py is a substituted or unsubstituted 2-, 3- or 4-pyridyl group. Further, of these, 2- and 3-pyridyl groups are preferred. The substituents which may be present include such common substituents as lower alkyl, hydroxy, alkoxy, aryloxy, aralkoxy, halogen, acyl, amino, nitro, carboxylic acid or salt, ester or amide derivatives of carboxylic acid groups. Preferably, if the pyridyl ring contains substituents these should be in the meta- or para-positions relative to the bond joining the ring to the group A. Preferably, also any such substituents should be carboxylic acid groups or groups which are converted in the human body to a carboxylic acid group or an acyl group. Examples of groups which are converted in the human body to carboxylic acid groups include salt, ester or amide derivatives of carboxylic acid groups, alkyl, alkenyl or alkynyl groups, (especially those having an odd number of carbon atoms), alkyl, alkenyl or alkynyl groups which carry hydroxy, alkoxy, aryloxy, aralkoxy, esterified hydroxy or carboxylic substituents, or a salt, ester or amide derivative of a carboxylic acid substituent.

We have noted a tendency for substituents in the 2-position of the phenyl ring to reduce the hypoglycaemic activity of the compounds of this invention. Thus, preferably, the groups $R_3$ and $R_4$ in compounds of formula (I) or (II) above are hydrogen.

To summarise what has been said above, of the compounds tested, we have noted that the majority of those having high activity fall within a fairly well defined sub-class. This preferred sub-class of compounds according to the invention consists of compounds of formula (VI) and acid addition salts thereof:-

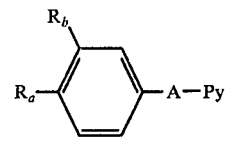

wherein Py represents a 2-, 3- or 4-pyridyl groups which is unsubstituted or is substituted in the meta-or-para-position (relative to the Py — A bond) by a carboxylic acid group or a salt, ester or amide derivatives of a carboxylic acid group or an alkyl group having an odd number of carbon atoms or an alkyl group having an even number of carbon atoms carrying a carboxylic acid substituent or a salt, ester or amide substituent; A represents a group of formula (IIIA), (IIIB) or (IIIC).

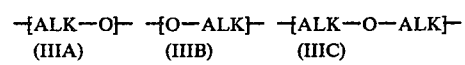

wherein ALK represents a straight chain alkylene group of from 1 to 6 carbon atoms (especially 1 to 3 carbon atoms) and $R_a$ and $R_b$ separately represent hydrogen or carboxylic acid groups or salt, ester or amide derivatives of carboxylic acid groups or alkyl groups having an odd number of carbon atoms or alkyl groups having an even number of carbon atoms and carrying carboxylic acid substituents or salt, ester or amide substituents, at least one of $R_a$ and $R_b$ not being hydrogen, provided that when Py is 2-pyridyl or 5-ethypyrid-2-yl and A is $[O-CH_2]$, neither $R_a$ nor $R_b$ is methyl or methoxycarbonyl.

Examples of compounds falling within the scope of the present invention which are particularly preferred for their high level of hypoglycaemic activity are the following, and their pharmaceutically acceptable acid addition salts:-
4-Methylphenoxy-3'-pyridylmethane
4-n-Propylphenoxy-2'-pyridylmethane
4-Methylbenzyloxy-2'-pyridylethane
1-(4-Methylbenzyloxy)-3-(2'-pyridyl)n-propane
4-Hydroxymethylphenoxy-2'-pyridylmethane
4-Carboxyphenoxy-2'pyridylmethane
4-Carboxymethylphenoxy-2'pyridylmethane
4-Carboxyethylphenoxy-2'-pyridylmethane
4-Carboxyethylethylenephenoxy-2'-pyridylmethane
4-β-Carboxyethylethylphenoxy-2'-pyridylmethane
4-Carbamylphenoxy-2'-pyridylmethane
4-Carbamylphenoxy-3'-pyridylmethane
4-Carbamylphenoxy-4'-pyridylmethane
4-Carboxyethylphenoxy-3'-pyridylmethane
3-(6-Methyl)pyridoxy-4'-methylphenylmethane
3-(6-Methyl)pyridoxy-4'-carboxyethylphenylmethane The acids which can be used to prepare acid addition salts of the compounds of this invention are suitably those which produce, when combined with the free base, salts whose anions are pharmaceutically acceptable. Examples of such acid addition salts are those derived from inorganic acids such as hydrochloric, hydrobromic, nitro, phosphoric, and sulphuric acids and from organic acids such as acetic, citric, malic, tartaric and lactic acids. When used in the form of its salt, the basic ether itself is the active portion of the molecule which produces the therapeutic effect, but by suitable choice of salt, the solubility, absorbtion or other properties of the compound may be varied.

The compounds of the present invention may be prepared by condensing a compound of formula (IV) with a compound of formula (V):

(IV) B — (ALK)$_n$OH     HO — (ALK)$_m$ —Py     (V)

wherein $n$ and $m$ are either 0 or 1, provided $n+m \neq 0$ and wherein the symobls ALK and Py are defined with respect to formula (I) or (II), and the symbol B represents a group of formula (IA) or (IIA)

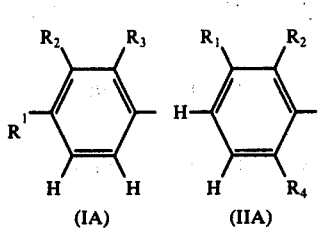

(IA)                (IIA)

wherein $R_1$, $R_2$, $R_3$ and $R_4$ are as defined with reference to formula (I) or (II).

The above condensation reaction may be effected with the aid of a condensing agent such as a carbodiimide (e.g. dicyclohexylcarbodiimide) or a carbonyldiimidazole. Alternatively a halide (e.g. chloride or bromide) of the compound of formula (IV) or (V) may be reacted with salt (e.g. the sodium or potassium salt) of the appropriate compound of formula (V) or (IV) respectively. Naturally it will be appreciated that it may be preferably to modify the substituents in the phenyl or pyridyl rings after the coupling reaction rather than before. Thus, it is preferable, when preparing compounds of formula (I) or (II) wherein $R_1$ or any of the other substituents is an amide or carboxylic acid group, first to prepare the corresponding compound wherein $R_1$ or the other substituents are carboxylic acid ester groups and then to convert such groups to carboxylic acid groups or amides or by conventional means. Further details of the overall preparation procedures used to prepare the compounds of this invention will become clear from the specific examples given below.

It has previously been mentioned that the compounds of this invention are hypoglycaemic agents and are thus useful in the preparation of pharmaceutical compositions for the treatment of diabetes mellitus. An added advantage of many of the compounds of this invention is that they are also hypolipidaemic agents. Since raised serum cholesterol and triglyceride levels are often found in diabetic patients this hypolipidaemic action is desirable.

The dose-response characteristics of the compounds of this invention vary from compound to compound. The more active of the compounds which we have tested cause a lowering of blood-sugar levels in alloxanised mice and normal mice when administered at dosages ranging from 30 to 300 mg/kg. In mice, rats, guinea pigs and squirrel monkeys, the hypoglycaemic activity of the compounds generally lasts over a period of from 2 to 6 hours. In the case of the compound which we have investigated most fully (4-carboxyethylphenoxy)-2'-pyridylmethane) a suitable dosage range for a human being is from 0.5 to 30 mg/kg/day, preferably about 5 mg/kg/day.

The compounds of this invention, especially 4-carboxyethylphenoxy-2'-pyridylmethane, have a different mode of action from the sulphonyl ureas since they do not cause insulin release. In common with the biguanides they inhibit glucose uptake from the small intestine but their effects on peripheral glucose utilisation are therapeutically more satisfactory. The preferred compounds are less likely to produce lactic acidosis than biguanides and are less likely to produce gastrointestinal irritation.

The following Examples illustrate the present invention:

EXAMPLE I

The following Table gives details of the structure and hypoglycaemic acitivity of a representative number of compounds. The hypoglycaemic acitivity was measured in alloxanised mice and scored by measuring the fall in bloodsugar caused by a dose of 300 mg/kg administrated intraperitoneally in carboxymethylcellulose.

Score Key
0 = < 5%
3 = 25-40%
1 = 5-15%
4 = <40%
2 = 15-25%

Details of the preparation of the compounds given in the table will be found in EXAMPLE 2 below.

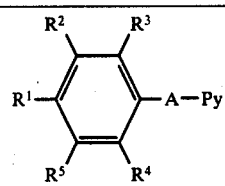

| Compound | A | R1 | R2 | R3 | R4 | R5 | Py | Hypoglycaemic Activity |
|---|---|---|---|---|---|---|---|---|
| 1 | 3-Methylphenoxy-2'-pyridylmethane Hydrochloride | —OCH$_2$— | H | CH3 | H | H | H | 2-pyridyl | 2 |
| 2 | 4-Methylphenoxy-2'-pyridylmethane Hydro- | —OCH$_2$— | CH3 | H | H | H | H | 2-pyridyl | 4 |

-continued

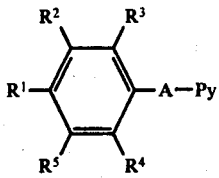

| Compound | A | R1 | R2 | R3 | R4 | R5 | Py | Hypo-glycaemic Activity |
|---|---|---|---|---|---|---|---|---|
| chloride | | | | | | | | |
| 3 4-Methyl-phenoxy-3¹-Pyridyl-methane | —OCH₂— | CH3 | H | H | H | H | 3-pyridyl | 4 |
| 4 4-Methyl-phenoxy-4¹-pyridyl-methane | —OCH₂— | CH3 | H | H | H | H | 4-pyridyl | 2 |
| 5 4-Ethyl-phenoxy-2¹-pyridyl-methane | —OCH₂— | CH3 | H | H | H | H | 2-pyridyl | 1 |
| 6 4-n-Propyl-phenoxy-2¹-pyridyl-methane | —OCH₂— | n-C₃H7 | H | H | H | H | 2-pyridyl | 3 |
| 7 4-Tert-butyl-phenoxy-2¹-pyridyl-methane | —OCH₂— | t-C₄H9 | H | H | H | H | 2-pyridyl | 2 |
| 8 2,3-Dimethyl-phenoxy-2¹-pyridyl-methane | —OCH₂— | H | CH3 | CH3 | H | H | 2-pyridyl | 2 |
| 9 2,5-Dimethyl-phenoxy-2¹-pyridyl-methane | —OCH₂— | H | CH3 | H | CH3 | H | 2-pyridyl | 2 |
| 10 2-Bromo-4-methyl-phenoxy-2¹-pyridyl methane | —OCH₂— | CH3 | H | Br | H | H | 2-pyridyl | 1 |
| 11 2-methoxy-4-methyl 2¹-pyridyl-methane | —OCH₂— | CH3 | H | CH₃O | H | H | 2-pyridyl | 2 |
| 12 4-Methyl-benzyloxy-2¹-pyridyl-methane | —CH₂OCH₂— | CH3 | H | H | H | H | 2-pyridyl | |
| 13 1-(4-Methyl-benzyloxy-)2-2-(2-pyridyl)-ethane | —CH₂OCH₂CH2 | CH3 | H | H | H | H | 2-pyridyl | 2 |
| 14 1-(4-Methyl-benzyl-oxy-3-(2¹-pyridyl)-n-propane | —CH₂OCH₂CH₂CH₂— | CH3 | H | H | H | H | 2-pyridyl | 3 |
| 15 4-Methyl-phenoxy-2¹-(6-methyl)-pyridyl-methane | —OCH₂— | CH3 | H | H | H | H | (6-methyl-2-pyridyl) | 1 |
| 16 4-Aceto-phenoxy-2¹-pyridyl-methane | —OCH₂— | CH₃CO— | H | H | H | H | 2-pyridyl | 2 |
| 17 4-Hydroxy-phenyl-phenoxy-2¹-pyridyl-methane | —OCH₂— | HOCH₂— | H | H | H | H | 2-pyridyl | 3 |
| 18 3-Carboxy-ethyl-phenoxy-2¹-pyridyl-methane | —OCH₂— | H | C₂H₅COO— | H | H | H | 2-pyridyl | 3 |
| 19 4-Carboxy-phenoxy-2¹-pyridyl-methane | —OCH₂— | —CO₂H | H | H | H | H | 2-pyridyl | 3 |
| 4-Carboxy- | | | | | | | | |

-continued

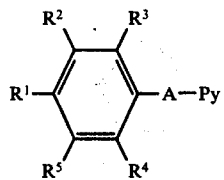

| Compound | A | R1 | R2 | R3 | R4 | R5 | Py | Hypoglycaemic Activity |
|---|---|---|---|---|---|---|---|---|
| 20 methylphenoxy-2¹-pyridylmethane | —OCH₂— | —CO₂CH₃ | H | H | H | H | 2-pyridyl | 3 |
| 21 4-Carboxyethylphenoxy-2¹-pyridylmethane | —OCH₂— | —CO₂C₂H₅ | H | H | H | H | 2-pyridyl | 4 |
| 22 4-Carboxy-n-propylphenoxy-2¹-pyridylmethane | —OCH₂— | —CO₂C₃H₇ⁿ | H | H | H | H | 2-pyridyl | 2 |
| 23 4-Carboxy-iso-propylphenoxy-2¹-pyridylmethane | —OCH₂— | —CO₂C₃H₇ⁱˢᵒ | H | H | H | H | 2-pyridyl | 2 |
| 24 4α-Carboxymethylphenoxy-2¹-pyridylmethane | —OCH₂— | —CH₂CO₂H | H | H | H | H | 2-pyridyl | 2 |
| 25 4-Carboxyethylenephenoxy-2'-pyridylmethane | —OCH₂— | —CH=CH—CO₂H | H | H | H | H | 2-pyridyl | 1 |
| 26 4-Carboxyethylethylenephenoxy-2¹-pyridylmethane | —OCH₂— | —CH=CH—CO₂C₂H₅ | H | H | H | H | 2-pyridyl | 3 |
| 27 4-β-Carboxyethylphenoxy-2¹-pyridylmethane | —O—CH₂— | —CH₂CH₂CO₂H | H | H | H | H | 2-pyridyl | 2 |
| 28 4-β-Carboxyethyl-ethyl-phenoxy-2¹-pyridylmethane | —OCH₂— | —CH₂CH₂CO₂C₂H₅ | H | H | H | H | 2-pyridyl | 4 |
| 29 4-Carbamylphenoxy-2¹-pyridylmethane hydrochloride | —OCH₂— | —CONH2 | H | H | H | H | 2-pyridyl | 3 |
| 30 4-Carbamylphenoxy-3¹-pyridylmethane | —OCH₂— | —CONH2 | H | H | H | H | 3-pyridyl | 4 |
| 31 4-Carbamylphenoxy-4¹-pyridylmethane hydrochloride | —OCH₂— | —CONH2 | H | H | H | H | 4-pyridyl | 3 |
| 32 4-(Ethoxyhippuryloxy)-2¹-pyridylmethane | —OCH₂— | —CONHCH₂CO₂C₂H₅ | H | H | H | H | 2-pyridyl | 2 |
| 33 4-(1-[3,5-Dimethyl pyrazole]-carbonylphenoxy-2¹-pyridyl methane | —OCH₂— | (3,5-dimethylpyrazol-1-yl)carbonyl | H | H | H | H | 2-pyridyl | 2 |

-continued

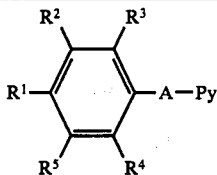

| Compound | A | R1 | R2 | R3 | R4 | R5 | Py | Hypoglycaemic Activity |
|---|---|---|---|---|---|---|---|---|
| 34 | 4-Carbonylhydrazino-phenoxy-2'-pyridylmethane | —OCH$_2$— | $\overset{O}{\overset{\|}{-C}}$—NHNH$_2$ | H | H | H | H | 2-pyridyl | 2 |
| 35 | 3-Carboxyethylphenoxy-4'-pyridylmethane | —OCH$_2$— | H | —CO$_2$C$_2$H$_5$ | H | H | H | 4-pyridyl | 4 |
| 36 | 2-Pyridoxy-4'-tolymethane | —CH$_2$O— | CH3 | H | H | H | H | 2-pyridyl | 1 |
| 37 | 3-Pyridoxy-4'-tolymethane | —CH$_2$O— | CH3 | H | H | H | H | 3-pyridyl | 3 |
| 38 | 3-(6-Methyl)-pyridoxy-4'-tolymethane | —CH$_2$O— | CH3 | H | H | H | H | CH$_3$—⟨pyridyl⟩ N= | 4 |
| 39 | 3-(6-Methyl)-pyridoxy-4'-carboxyethyl-phenyl-methane | —CH$_2$O— | CO$_2$C$_2$H$_5$ | H | H | H | H | CH$_3$—⟨pyridyl⟩ N= | 4 |
| 40 | 4-Methylphenoxy-2'-pyridylmethane N-Oxide hydrochloride | —OCH$_2$— | —CH3 | H | H | H | H | ⟨pyridyl N→O⟩ | 2 |
| 41 | 4-Methylphenoxy-1'-methylenecarbethoxy-pyridinium-2'-yl methane bromide | —OCH$_2$— | CH3 | H | H | H | H | ⟨N⁺-CH$_2$CO$_2$C$_2$H$_5$⟩ Br⁻ | 2 |
| 42 | 4-Carboxyethylphenoxy-3'-pyridylmethane Hydrochloride | —OCH$_2$— | C$_2$H$_5$OCO— | H | H | H | H | 3-pyridyl | 3 |

EXAMPLE 2 a. Preparation of 4-Carbethoxyphenoxy-2'-pyridylmethane

Phosphorus oxychloride (15g) was added with stirring to 2-hydroxymethylpyridine (17.5g) in ethyl acetate (80ml) at 0° C. The mixture was heated on a water bath for 1 hour and allowed to stand at room temperature for 5 hours. The solvent was distilled off under reduced pressure to give a residue which was dissolved in water and the solution made alkaline with aqueous sodium carbonate. The resulting oil was extracted into ether; the ether extracts were washed twice with water, dried over MgSO$_4$, the solvent was removed by distillation and the residue fractionated to give 2-chloromethylpyridine (14.5g; 71%). Ethyl-4-hydroxybenzoate (19.6 g) in ethanol (100ml) followed by 2-chloromethylpyridine (15.0g) was added to a solution of sodium (2.8g) in ethanol (100ml) and the mixture refluxed for 4 hours. On cooling, the NaCl was filtered off and the solvent distilled off under reduced pressure to give a solid product which was recrystallised from ethanol. This was 4-carboxyethylphenoxy-2'-pyridylmethane (16.7g; 55%). M.pt 78° C.

4-Carboxyethylphenoxy-2'-pyridylmethane
I.R. Vmax (KBr) 2991, 1710, 1270, 767 cm$^{-1}$.
N.M.R. T:- 1.37 d. (J. 4 Hz., 1 aromatic proton); 1.9–3. M. (7 × aromatic proton); 4.75 S. (CH$_2$); 5.65 q (J. 8 Hz., —OCH$_2$CH$_3$); 8.64 t (J. 8HZ., 0—CH$_2$CH$_3$) in CDCl$_3$.

Following the above procedure (i.e. reaction of the sodium salt of the appropriate pyridine derivative with the chloride of the appropriate hydroxybenzoate, compounds 1, 2, 3, 4, 5, 6, 7, 8, 9, 10, 11, 15, 16, 18, 20, 22, 23, 26, 28, 35 and 42 were prepared. Elemental analyses, infra-red spectra, proton magnetic resonance spectra confirmed the structures.

b). Preparation of 4-Carboxyphenoxy-2'-pyridylmethane

4-Carboxyethylphenoxy-2'-pyridylmethane (2g) was refluxed with 20% aqueous sodium hydroxide (50ml) for 4 hours. The solution was cooled, acidified with glacial acetic acid and the precipitated solid filtered off. It was then dried and recrystallised from ethanol to give 1.6g (90%) of 4-carboxyphenoxy-2'-pyridylmethane. M.pt 214° C.

4-Carboxyphenoxy-2'-pyridylmethane

I.R. Vmax (KBr) 1690, 1600, 1260, 768 cm$^{-1}$.
N.M.R. T:- 1.4 d. (J. 4 Hz., 1 aromatic proton); 2–3 M. (7 × arcmatic proton); 4.75 S ($CH_2$) in $(CD_3)_2SO$.

Following the above procedure (i.e. alkaline hydrolysis of the appropriate ethyl ester), the following compounds were prepared:- 19, 24, 25, and 27. Again elemental analysis, infra-red spectra and proton magnetic resonance spectra confirmed the structures.

c. Preparation of 3-(6-Methyl)pyridoxy-4-tolylmethane.

3-Hydroxy-6-methylpyridine (5.5g) in ethanol (150ml) followed by p-ethylbenzyl chloride (7.1g) was added to a solution of sodium (1.2g) in ethanol and the mixture refluxed for 5 hours. After cooling the sodium chloride was filtered off and the solvent distilled off under reduced pressure to give a solid product. This was recrystallised from ethanol to give 4.6g (42%) of 3-(6-methyl)pyridoxy-4-tolylmethane, m.pt 71° C.

3-(6-Methyl) pyridoxy-4'-methylphenylmethane

I.R. Vmax (KBr) 2920, 1255, 1010, 810 cm$^{-1}$.
N.M.R. T:- 1.75 d. (J. 3 Hz., 1 aromatic proton); 2.58–2.97 M. (6 × aromatic proton); 4.88 S. CH$_2$); 5.60 q. (J. 8 HZ., —OCH$_2$CH$_3$); 7.50 S. (CH$_3$); 8.62 t. (J. 8 Hz., O—CH$_2$—CH$_3$) in CDCl 3.

Following the above procedure compounds 36 and 37 were prepared. Infra-red spectra, proton magnetic resonance spectra and elemental analyses confirmed the structures.

d. 4-Carbamylphenoxy-2'-pyridylmethane hydrochloride

4-Hydroxybenzamide (13.7g) were dissolved in 150 mls of isopropyl alcohol containing 2.3g sodium at 60° C. 14g of 2-picolyl chloride was added to the solution and the mixture left for 5 hours at 100° C. The solvent was then distilled off and the residue dissolved in ethanol. The insoluble material was filtered off and the alcohol evaporated. The residue was then dissolved in 2N HCl and the solution decolourised with charcoal. The solution was evaporated to dryness and the residue recrystallised twice from ethanol.

This gave 17.8g (67.5%) of required compound, m.pt 208°–210° C.

Following the above procedure, compounds 30 and 31 were prepared. Elemental analysis, infra-red spectra and proton magnetic resonance spectra confirmed the structures.

e. 4-Carbonylhydrazinophenoxy-2'-pyridylmethane

4-Carboxyethylphenoxy-2'-pyridylmethane (3 g) and hydrazine hydrate (10 ml) were refluxed together in ethanol (20 ml). The hot solution was filtered, allowed to cool and the solid which crystallised out was filtered off, dried and recrystallised from ethanol. This gave 2.00 g (71%) 4-Carbonylhydrazinophenoxy-2'-pyridylmethane. M.P.T. 185°–186° C.

4-Carbonylhydrazionphenoxy-2'-pyridylmethane
I.R. (KBr) 3360, 1620, 1600, 760 cm$^{-1}$.
N.M.R. T:- 0.4 S. (NH), 1.37 d. (J. 4 Hz., 1 aromatic proton); 2.1–3 M. (7 x aromatic proton); 4.75 S (CH$_2$); 5.55 S. (NH$_2$) in (CD$_3$)$_2$SO.

f. 4-(1-[3,5-Dimethylpyrazole]) carbonylphenoxy-2'-pyridylmethane

4-Carbonylhydrzinophenoxy-2'-pyridylmethane (3.58 g) and acetylacetone (1.5 ml) were refluxed together in ethanol (100 ml) for 3 hours. The solvent was evaporated to dryness and the product recrystallised from petroleum ether (60–80). This gave 1.26 g (28%) 4-(1-[3,5-Dimethylpyrazole]) carbonylphenoxy-2'-pyridylmethane. M.P.T. 106° C.

4-(1-[3,5-Dimethylpyrazole])carbonylphenoxy-2''-pyridylmethane

I.R. (KBr) 1700, 1345, 926, 758 cm$^{-1}$.
N.M.R. T:- 1.4–3.07 M. (8 x aromatic proton); 3.98 S. (CH); 4.74 S. (CH$_2$); 7.4 S. (CH$_3$); 7.80 S. (CH$_3$) in CDCl$_3$.

g. 4-(Ethoxyhippuryloxy)-2'-pyridylmethane

Glycinethylester hydrochloride (3.50 g) was suspended in dichloromethane (75 ml), triethylamine (3.4 ml) added and the mixture stirred for 5 minutes. The reaction mixture was filtered and 4-carboxyphenoxy-2'-pyridylmethan (5.70 g) and dicyclohexylcarbodiimide (5.10 g) added to the filtrate. The reaction mixture was stirred at room temperature for 16 hours. The insoluble material was filtered off, the solvent evaporated to dryness and the product recrystallised from ethanol. This gave 3.5 g (49%) 4-(Ethoxyhippuryloxy)-2'-pyridylmethane. M.P.T. 107°–108° C.

4-(Ethoxyhippuryloxy)-2'-pyridylmethane

I.R. Vmax (KBr) 3275, 2900, 1740, 1500, 855, 772 cm$^{-1}$. N.M.R. T:- 1.35–3 M. (8 × aromatic proton); 4.75 S. (CH$_2$); 5.87 q. (J. 8 Hz., O—CH$_2$—CH$_3$); NH overlapped in q at 5.87 T.; 6.72 S (CH$_2$); 8.8 t. (J. 8 Hz., O—CH$_2$CH$_3$) in (CD$_3$)$_2$SO.

3-(6-Methyl)-pyridoxy-4'-carboxyethyl phenylmethane

Ethyl-p-toluate (23.68 g), N-bromosuccinimide and -azobutyronitrile (0.05 g) were refluxed together in carbontetrachloride for 2 hours. The reaction mixture was cooled, the solid filtered off and the solvent evaporated to give p-carboxyethylbenzylbromide (36.05 g). p-Carboxyethylbenzylbromide (13.7g) was added to a solution of 3-hydroxy-6-methylpyridine (6.2 g) in ethanol (130 ml) containing sodium (1.3 g). The solution was refluxed for 3 hours, cooled, the sodium chloride filtered off, the solvent evaporated to dryness and the product recrystallised from petroleum ether (60–80). This gave 8.4 g (53%) 3-(6-Methyl)-pyridoxy-4'-carboxyethyl phenylmethane. M.P.T. 61° C.

i. 1-(4-Methylbenzyloxy)-2-(2''-pyridyl)ethane 2-(2-Hydroxyethyl) pyridine (13 g) were dissolved in methane (50 mls) containing sodium (2.3 g) and the solution evaporated to dryness under vacuum. The resulting sodium salt was suspended in toluene 50 mls and -bromo-p- (24 g) was added, and the mixture leveled at 100° C. for 5 hours. The solution was cooled, the which filtered off and the solvent removed under vacuum. The residue was dissolved in 2N HCl and extracted with ethyl acetate. The aqueous layer was made alkaline with potassium carbonate solution and extracted with ethyl acetate. The ethyl acetate layer was washed with water, dried so the solvent removed and the residue distilled under vacuum.

This gave 3 g (14.8%) of title compound.
BPT. 115°–118° C /0.15mins.
1-(4-Methylbenzyloxy)-2(2"pyridyl) ethane
I.R. Vmax (KBr) 2860, 1593, 1095, 805, 755 cm$^{-1}$.
N.M.R. T:- 1.52 d. (J. 4 Hz., 1 aromatic proton) 2.4–3.1 M (7 × aromatic proton); 5.55 S (CH$_2$); 6.15 t (J. 7 Hz - CH$_2$—CH$_2$); 6.9 t. (J. 7 Hz - CH$_2$CH$_2$—); 7.75 S. (CH$_3$) in CDCl$_3$.

| Elemental analysis. | | | |
|---|---|---|---|
| Theoretical | 79.29% C | 7.48% H | 6.17% N |
| Found | 78.62% C | 7.40% H | 5.60% N |
| Found | 78.46% C | 7.59% H | 5.97% N |

Following the above procedure, compounds 12 and 14 were prepared. Elemental analysis, infra-red spectra and proton magnetic resonance spectra confirmed the structures.

j. 4-Methylphenoxy-2'-pyridylmethane N-Oxide Hydrochloride

4-Methylphenoxy-2'-pyridylmethan (5 g) was suspended in acetic acid (10 mls) and 30% hydrogen peroxide (3.8 mls). The solution was heated at 70° C for 24 hours. After cooling the solid was filtered off, washed with acetic acid and recrystallised from ethanol by addition of ether. This gave 5.5 g (87%) of the title compound m.pt 126°–127°.

k. 4-Methylphenoxy-1'-methylenecarbethoxy pyridinium-2'-ylmethane bromide.

4-Methylphenoxy-2'-pyridylmethane (1.9 g) and ethyl bromoacetate (1.7 g) were heated at 80° C for 4 hours in nitropropane (20 mls). The solution was then cooled and filtered, the solid washed with ether and dried in vacuu to give 2.3 g (63%) of title compound, m.pt 187°–192° C.

EXAMPLE 3

From the list of compounds in the Table in Example 1 a number were selected for examination of hypoglycaemic activity in normal mice, the compound being administered by the oral and intraperitoneal routes, and toxicity studies. The compounds examined in this way were nos. 2, 3, 6, 8, 11, 16, 19, 20, 21, 32, 38 and 42.

After examination of the results achieved with these compounds, compound no. 21 (4-carboxyethylphenoxy-2'-pyridylmethane) was chosen for further evaluation. The compound is notable for its low order of oral toxicity, but useful hypoglycaemic activity at low doses, i.e. the compound has a very good therapeutic ratio. Further biological data for the compound is given in the Table below.

| Species | Dose mg/kg | Route | % Blood glucose lowering after time t | t hours |
|---|---|---|---|---|
| Alloxanised mice | 300 | IP | 37 | 2 |
| Normal mice | 300 | 0 | 50 | 6 |
| Normal rat | 300 | 0 | 32 | 6 |
| Normal guinea pig | 300 | 0 | 64 | 2 |
| Squirrel monkey | 100 | 0 | 30 | 1 |
| Beagle dog | 250 | 0 | 25 | Repeat dose |

Key
0 = Oral
IP = Intraperitoneal

We claim:
1. A compound of the formula

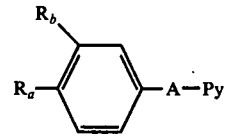

or a pharmaceutically acceptable non-toxic acid addition salt thereof, wherein Py is 3- or 4-pyridyl unsubstituted or meta- or -para-lower alkyl substituted A is ─[ALK-O]─or─[ALK-O-ALK]─wherein ALK is straight or branched chain alkylene of 1 to 6 carbon atoms, only one of R$_a$ and R$_b$ is hydrogen and the other is selected from the group consisting of carboxy, carboloweralkoxy, cyano and carbamyl.

2. A compound of claim 1 wherein ALK is of 1 of 3 carbon atoms.

3. The compound 4-β-carboxyethylenephenoxy-2'-pyridylmethane or a pharmaceutically acceptable non-toxic acid addition salt thereof.

4. The compound 4-carbamylphenoxy-3'-pyridylmethane or a pharmaceutically acceptable non-toxic acid addition salt thereof.

5. The compound 3-(6-methyl)-pyridoxy-4'-carboxyethylphenylmethane.

6. The compound 3-(6-methyl)-pyridoxy-4'-methylphenylmethane.

7. The compound 3-carboxyethyl-phenoxy-4'pyridylmethane.

8. A compound according to claim 1 wherein Py is 3- or 4-pyridyl, meta- or para-lower alkyl substituted.

* * * * *

UNITED STATES PATENT AND TRADEMARK OFFICE
CERTIFICATE OF CORRECTION

PATENT NO. : 4,036,844
DATED : July 19, 1977
INVENTOR(S) : Thorne, et al.

It is certified that error appears in the above-identified patent and that said Letters Patent are hereby corrected as shown below:

Page 1, second item under heading of "Foreign Application Priority Data" delete -- Dec. 23, 1974 United Kingdom 55441/74

Signed and Sealed this

Twenty-fifth Day of October 1977

[SEAL]

Attest:

RUTH C. MASON
Attesting Officer

LUTRELLE F. PARKER
Acting Commissioner of Patents and Trademarks